US012594407B2

(12) United States Patent
Lu et al.

(10) Patent No.: US 12,594,407 B2
(45) Date of Patent: *Apr. 7, 2026

(54) PREPARATION DELIVERY ASSEMBLY AND DEVICE HAVING MULTIPLE NEEDLES

(71) Applicants: BEIJING BOE TECHNOLOGY DEVELOPMENT CO., LTD., Beijing (CN); BOE TECHNOLOGY GROUP CO., LTD., Beijing (CN)

(72) Inventors: Yongchun Lu, Beijing (CN); Hui Li, Beijing (CN); Pan Li, Beijing (CN); Chunping Long, Beijing (CN)

(73) Assignees: BEIJING BOE TECHNOLOGY DEVELOPMENT CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 966 days.

This patent is subject to a terminal disclaimer.

(21) Appl. No.: 17/807,224

(22) Filed: Jun. 16, 2022

(65) Prior Publication Data

US 2022/0305246 A1 Sep. 29, 2022

Related U.S. Application Data

(63) Continuation of application No. 16/831,100, filed on Mar. 26, 2020, now Pat. No. 11,413,441.

(30) Foreign Application Priority Data

Aug. 22, 2019 (CN) .......................... 201910782978.0

(51) Int. Cl.
A61M 37/00 (2006.01)
G03F 7/00 (2006.01)
(52) U.S. Cl.
CPC ....... A61M 37/0015 (2013.01); G03F 7/0035 (2013.01); *A61M 2037/0023* (2013.01);
(Continued)

(58) Field of Classification Search
CPC .......... A61M 5/14224; A61M 5/14586; A61M 5/14593; A61M 37/0015–2037/0061;
(Continued)

(56) References Cited

U.S. PATENT DOCUMENTS

| | | | | |
|---|---|---|---|---|
| 3,007,416 A | * | 11/1961 | Childs ................. | A61M 60/427 251/5 |
| 5,527,288 A | * | 6/1996 | Gross ................ | A61M 5/14593 604/145 |

(Continued)

FOREIGN PATENT DOCUMENTS

| | | | | |
|---|---|---|---|---|
| CA | 3146663 A1 | * | 1/2021 | ............. A61N 1/327 |
| CN | 1190904 A | | 8/1998 | |

(Continued)

OTHER PUBLICATIONS

First Office Action for Chinese Application No. 201910782978.0, dated Mar. 3, 2021, 2017, 9 Pages.

(Continued)

*Primary Examiner* — Nathan R Price
(74) *Attorney, Agent, or Firm* — BROOKS KUSHMAN P.C.

(57) ABSTRACT

A preparation delivery assembly includes: a first substrate, a second substrate, and at least two needles of different lengths. Two side walls are provided between the first and second substrates to define a first chamber. At least one first channel that is in communication with the first chamber is provided in the second substrate in a direction perpendicular to the second substrate. And the needles are arranged on a surface of the second substrate, and each needle is in communication with the first chamber to deliver the preparation. A third channel is provided in the first substrate in a direction perpendicular to the first substrate, and one end of the third channel is in communication with the first chamber (Continued)

so as to guide the preparation introduced from the other end of the third channel into the first chamber.

15 Claims, 3 Drawing Sheets

(52) U.S. Cl.
CPC .................. *A61M 2037/003* (2013.01); *A61M 2037/0053* (2013.01); *A61M 2205/3368* (2013.01); *A61M 2205/3606* (2013.01)

(58) Field of Classification Search
CPC .............. A61M 5/3295; A61M 5/3298; A61M 2025/0085–0087; A61M 60/268
See application file for complete search history.

(56) References Cited

U.S. PATENT DOCUMENTS

| | | | |
|---|---|---|---|
| 6,132,755 A | 10/2000 | Eicher et al. | |
| 6,256,533 B1 | 7/2001 | Yuzhakov et al. | |
| 6,605,066 B1 * | 8/2003 | Gravagna | A61B 17/00491 |
| | | | 604/82 |
| 2002/0138049 A1 | 9/2002 | Allen et al. | |
| 2003/0135158 A1 | 7/2003 | Gonnelli | |
| 2007/0078376 A1 | 4/2007 | Smith | |
| 2007/0088348 A1 * | 4/2007 | Kochamba | A61M 5/14248 |
| | | | 606/41 |
| 2008/0009800 A1 | 1/2008 | Nickel | |
| 2008/0161772 A1 * | 7/2008 | Nayak | A61M 5/19 |
| | | | 604/506 |
| 2012/0046644 A1 | 2/2012 | Ziaie et al. | |
| 2017/0007812 A1 * | 1/2017 | Onozuka | A61M 37/0015 |
| 2020/0001064 A1 | 1/2020 | Alary et al. | |

FOREIGN PATENT DOCUMENTS

| | | |
|---|---|---|
| CN | 1608686 A | 4/2005 |
| CN | 101068591 A | 11/2007 |
| CN | 101829394 A | 9/2010 |
| CN | 101879336 A | 11/2010 |
| CN | 106110491 A | 11/2016 |
| JP | 2015226649 A | 12/2015 |
| WO | 2006037825 A1 | 4/2006 |
| WO | 2011116388 A1 | 9/2011 |

OTHER PUBLICATIONS

Restriction Requirement for U.S. Appl. No. 16/831,100, dated Aug. 16, 2021, 5 Pages.
Non-Final Rejection for U.S. Appl. No. 16/831,100, dated Dec. 22, 2021, 12 Pages.

* cited by examiner

PREPARATION DELIVERY ASSEMBLY AND DEVICE HAVING MULTIPLE NEEDLES

CROSS-REFERENCE TO RELATED APPLICATIONS

This application is a continuation of U.S. patent application Ser. No. 16/831,100 filed on Mar. 26, 2020, which claims priority to Chinese Patent Application No. 201910782978.0 filed on Aug. 22, 2019, which are incorporated herein by reference in their entireties.

TECHNICAL FIELD

The present disclosure relates to the field of microfluidic chips, and in particular, to a preparation delivery assembly and device, and a method for fabricating a needle array in the assembly.

BACKGROUND

A minimally invasive (microneedle) transdermal drug delivery system can work by delivering a given preparation to a systemic circulation through skin via capillaries. As compared with traditional methods, a minimally invasive transdermal drug delivery method has many advantages, such as minimal invasion, and tiny channels opened in the skin due to a small needle diameter; no pain and no risk of bleeding because of only penetration of a stratum corneum to reach a dermal layer by needles without reaching nerves and blood vessels; and targeting, which can be achieved by designing heights of the needles and controlling the position of the needles in the skin.

However, a diffusion range of the preparation from the preparation delivery assembly in related minimally invasive transdermal drug delivery systems is limited, resulting in a poor absorption effect of the preparation and a poor user experience.

SUMMARY

In a first aspect, embodiments of the present disclosure provide a preparation delivery assembly including: a first substrate, a second substrate, and at least two needles of different lengths, each of which is a hollow needle having a hollow structure; wherein two side walls are provided between the first substrate and the second substrate to define a first chamber for containing a preparation by the first substrate, the second substrate, and the two side walls; at least one first channel that is in communication with the first chamber is provided in the second substrate in a direction substantially perpendicular to the second substrate; and the needles are arranged on a surface of the second substrate distal to the first substrate, and each of the needles is in communication with the first chamber through the at least one first channel to deliver the preparation.

According to some optional embodiments of the present disclosure, the first channel includes a plurality of sub-channels, each of which corresponds to one or more needles of one length of the at least two needles of different lengths.

According to some optional embodiments of the present disclosure, the assembly further includes a temperature control circuit configured to sense a temperature of the preparation contained in the first chamber, and adjust the temperature of the preparation when it is outside an allowable range.

According to some optional embodiments of the present disclosure, at least one of the first and second substrates is made of a flexible material.

According to some optional embodiments of the present disclosure, at least one recess is provided on a surface of the first substrate proximal to the second substrate, and an elastic isolation membrane is provided between the recess and the first chamber to define a second chamber by the recess and the elastic isolation membrane; and a second channel is further provided in the first substrate in a direction substantially parallel to the first substrate, and one end of the second channel is in communication with the second chamber, and the other end of the second channel is in communication with the outside so as to introduce air from the outside into the second chamber.

According to some optional embodiments of the present disclosure, the number of the recesses is greater than one.

According to some optional embodiments of the present disclosure, the other end of the second channel is provided with a valve to control a flow volume of the air entering the second chamber from the outside.

According to some optional embodiments of the present disclosure, a third channel is provided in the first substrate in a direction substantially perpendicular to the first substrate, and one end of the third channel is in communication with the first chamber so as to guide the preparation introduced from the other end of the third channel into the first chamber.

According to some optional embodiments of the present disclosure, an inner wall of the needle and the surface of the second substrate distal to the first substrate are substantially perpendicular to each other.

According to some optional embodiments of the present disclosure, hydrophilicity and hydrophobicity of the inner wall of the needle match those of the preparation.

According to some optional embodiments of the present disclosure, the needles of different lengths have different inner diameters.

According to some optional embodiments of the present disclosure, inner diameters of the needles are in a range of 10 micrometers to 80 micrometers.

According to some optional embodiments of the present disclosure, distances between the respective needles range from 100 micrometers to 500 micrometers.

According to some optional embodiments of the present disclosure, the lengths of the needles are in a range of 25 micrometers to 1000 micrometers.

According to some optional embodiments of the present disclosure, a lateral side of a cross section of the needle taken in a direction perpendicular to the surface of the first or second substrate has an inclination angle of 10 degrees to 25 degrees with respect to a normal direction of the surface of the first or second substrate.

In a second aspect, embodiments of the present disclosure further provide a preparation delivery device including a preparation delivery assembly, and a storage portion for storing a preparation, which is in communication with the preparation delivery assembly to supply the preparation to the preparation delivery assembly. The assembly includes a first substrate, a second substrate, and at least two needles of different lengths, each of which is a hollow needle having a hollow structure; wherein two side walls are provided between the first substrate and the second substrate to define a first chamber for containing a preparation by the first substrate, the second substrate, and the two side walls; at least one first channel that is in communication with the first chamber is provided in the second substrate in a direction substantially perpendicular to the second substrate; and the needles are arranged on a surface of the second substrate distal to the first substrate, and each of the needles is in communication with the first chamber through the first channel to deliver the preparation.

In a third aspect, embodiments of the present disclosure further provide a method for fabricating one or more needle arrays in a preparation delivery assembly, including: depositing a protective film on at least one of a first side and a second side of a substrate sheet; forming, through a first patterning process, a pattern of the needle array(s) on the protective film deposited on the at least one of the first side and the second side of the substrate sheet; forming a shape of the needle array(s) on the substrate sheet through a second patterning process with the formed pattern of the needle array(s) as a mask; removing the protective film which has the formed pattern of the needle array(s) and which has been used as the mask; and performing ion bombardment on the substrate sheet, which has the shape of the needle array(s) and from which the protective film has been removed, by controlling an intensity and time of ion bombardment in each predetermined area, so as to form the needle arrays of different heights.

According to some optional embodiments of the present disclosure, after performing the ion bombardment on the substrate sheet, which has the shape of the needle array(s) and from which the protective film has been removed, by controlling the intensity and time of ion bombardment in each predetermined area, so as to form the needle arrays of different heights, the method further includes: treating surfaces of the needles in the needle array(s) by using at least one of an oxygen plasma treatment and a chemical surface treatment to make hydrophilicity and hydrophobicity of an inner wall of each of the needles match those of the preparation.

According to some optional embodiments of the present disclosure, after depositing the protective film on the at least one of the first side and the second side of the substrate sheet, the method further includes: applying a liquid or dry film photoresist on the at least one of the first side and the second side of the substrate sheet, on which the protective film has been deposited, and drying the photoresist to form a film.

According to some optional embodiments of the present disclosure, the photoresist is removed using a NaOH or KOH solution; and the protective film, which has the formed pattern of the needle array(s) and which has been used as the mask, is removed by using wet cleaning or dry etching to form the needle arrays of different heights.

BRIEF DESCRIPTION OF THE DRAWINGS

In order to illustrate the technical solutions of the embodiments of the present disclosure more apparently, the accompanying drawings required in the description of the embodiments of the present disclosure will be briefly introduced below. It is evident that the drawings used in the following description relate to only some embodiments of the present disclosure, and based on these drawings, the other drawings can be obtained by those of ordinary skill in the art without exercising any inventive work.

DETAILED DESCRIPTION

In order to make the objects, technical solutions, and advantages of the embodiments of the present disclosure more apparent, the technical solutions of the embodiments of the present disclosure will be clearly and completely described hereinafter with reference to the accompanying drawings for the embodiments of the present disclosure. Obviously, the described embodiments are a part, rather than all, of the embodiments of the present disclosure. Based on the described embodiments of the present disclosure, all the other embodiments obtained by those of ordinary skill in the art fall within the protection scope of the present disclosure.

Technical or scientific terms used in the present disclosure shall have ordinary meanings understood by those having ordinary skills in the art to which the present disclosure pertains, unless otherwise defined. The terms "first", "second", and the like used herein are not intended to indicate any order, quantity, or importance, but are only used to distinguish different components from each other. The terms "including", "comprising", etc. are intended to specify that the elements or items stated before these terms encompass the elements or items and equivalents thereof listed after these terms, but do not preclude the other elements or items. The phrases "connected", "connecting", etc. are not intended to define a physical or mechanical connection, but may include an electrical connection, either direct or indirect. The terms "up", "down", "left", "right", etc., are merely used to indicate a relative positional relationship, and if the absolute position of the described object is changed, the relative positional relationship will be changed accordingly.

In order to keep the following description of the embodiments of the present disclosure clear and concise, detailed descriptions of known functions and components are omitted in the present disclosure.

Figure 1:
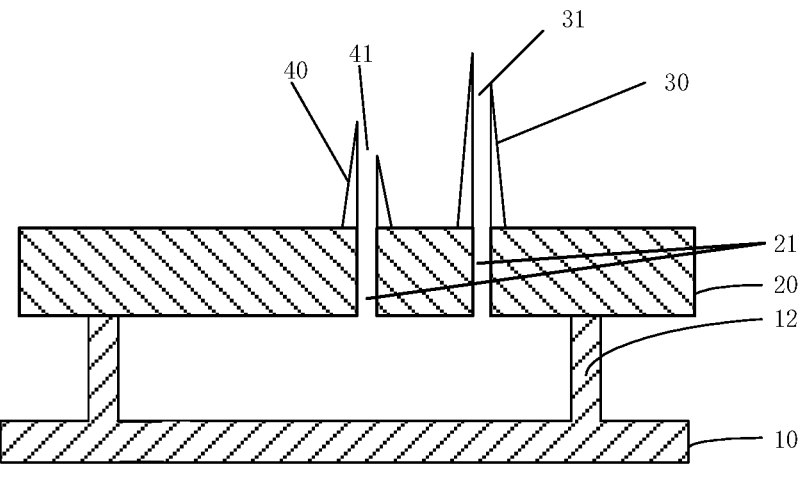
FIG. 1 is a first schematic diagram showing a sectional structure of a preparation delivery assembly according to a first embodiment of the present disclosure.

A first embodiment of the present disclosure provides a preparation delivery assembly, of which a schematic sectional structure is shown in FIG. 1. The assembly includes: a first substrate 10, a second substrate 20, and at least two needles of different lengths (FIG. 1 shows only one needle of each length as an example, that is, 30 and 40), each of which is a hollow needle having a hollow structure. Two side walls 12 are provided between the first substrate 10 and the second substrate 20 such that the first substrate 10, the second substrate 20, and the two side walls 12 define a first chamber for containing a preparation. At least one first channel 21 that is in communication with the first chamber is provided in the second substrate 20. Specifically, as shown in FIG. 1, at least one first channel 21 that is in communication with the first chamber is provided in the second substrate 20 in a direction substantially perpendicular to the second substrate 20. Here, the number of the first channels 21 provided may be the same as the number of the needles (that is, in one-to-one correspondence), or, they may be different. For example, one needle communicates with the first chamber through a plurality of first channels 21. The needles are arranged on a surface of the second substrate 20 distal to the first substrate 10, and each of the needles communicates with the first chamber through the first channel 21 to deliver the preparation.

FIG. 1 shows only an example, which can be set, supplemented or modified by those skilled in the art according to actual requirements.

The preparation delivery assembly in a minimally invasive transdermal drug delivery system in the related art has only needles of one length (that is, an array of needles having a same height), and the diffusion range of the preparation is limited after reaching a designated depth, which results in poor absorption of the preparation. However, the preparation delivery assembly according to the embodiment of the present disclosure is provided with at least two needles of different lengths, which can reach different depths of the dermal layer, thereby realizing multi-point simultaneous delivery of the preparation. After the diffusion of the preparation at different depths, a wider range of diffusion can be achieved, so that the preparation can be better absorbed, and the use effect is better.

Figure 2:
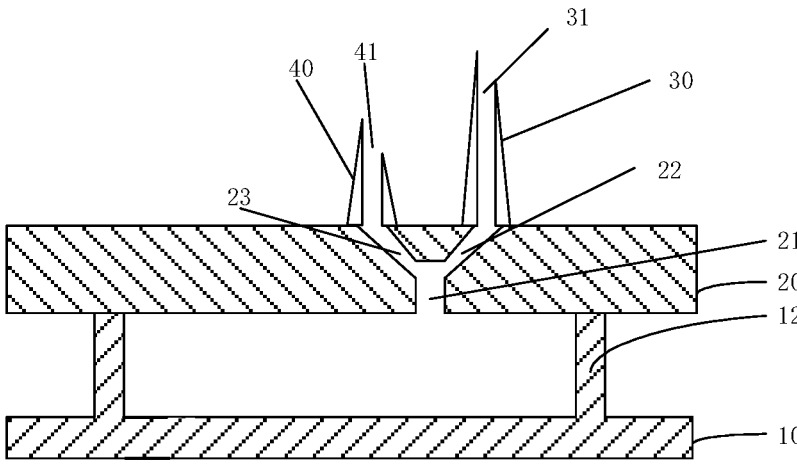
FIG. 2 is a second schematic diagram showing a sectional structure of the preparation delivery assembly according to the first embodiment of the present disclosure.

In a specific implementation, the first channel 21 may include a plurality of sub-channels (22 and 23 shown in FIG. 2), each of which corresponds to one or more needles of a same length, and its structure can be schematically shown in FIG. 2. The delivery of the preparation through the plurality of sub-channels of one first channel 21 enables more uniform delivery of the preparation of each needle. FIG. 2 still shows an example in which the preparation delivery assembly includes only two needles of different lengths. In a specific implementation, the number of the first channel may be greater than one, and each first channel may be provided with one corresponding needle, or with a corresponding set of needles having a same length. Alternatively, each of the sub-channels of the first channel may be provided with one corresponding needle, or with a plurality of corresponding needles having a same length. A specific configuration can be designed by a person skilled in the art and is not limited to those described herein.

Figure 3:
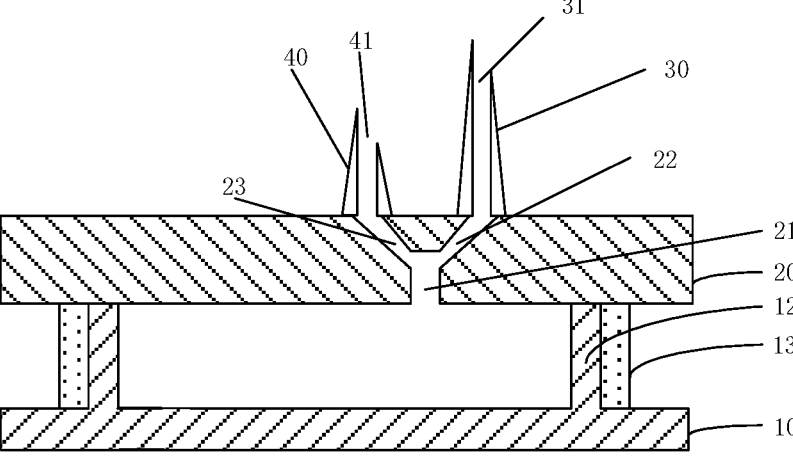
FIG. 3 is a third schematic diagram showing a sectional structure of the preparation delivery assembly according to the first embodiment of the present disclosure.

The preparation delivery assembly may further include a temperature control circuit 13 configured to sense a temperature of the preparation contained in the first chamber, and adjust the temperature of the preparation when it is outside an allowable range, as shown in FIG. 3.

In a first specific implementation, the temperature control circuit 13 may include a temperature sensor for monitoring the temperature of the preparation in the first chamber in real time, and a refrigeration component for regulating (i.e., reducing) the temperature of the preparation in the first chamber when an ambient temperature exceeds, for example, 35 degrees Celsius, so as to ensure that the preparation in the assembly is in an injectable fluid state. Here, as understood by those skilled in the art, it is assumed in the first specific implementation that the preparation of the first chamber stays in a liquid state when it is lower than 35 degrees Celsius.

However, a critical temperature of the preparation in the first chamber kept in the liquid state varies with the type of the preparation. In a second specific implementation, it is assumed that preparations in the first chamber are in the liquid state when they are higher than, for example, 10 degrees Celsius. In the second specific implementation, the temperature control circuit 13 may include a temperature sensor for monitoring the temperature of the preparation in the first chamber, and a heating component for regulating (i.e., increasing) the temperature of the preparation in the first chamber when the ambient temperature is lower than, for example, 10 degrees Celsius, so as to ensure that the preparation in the assembly is in an injectable fluid state.

Figures 4, 5, 6:
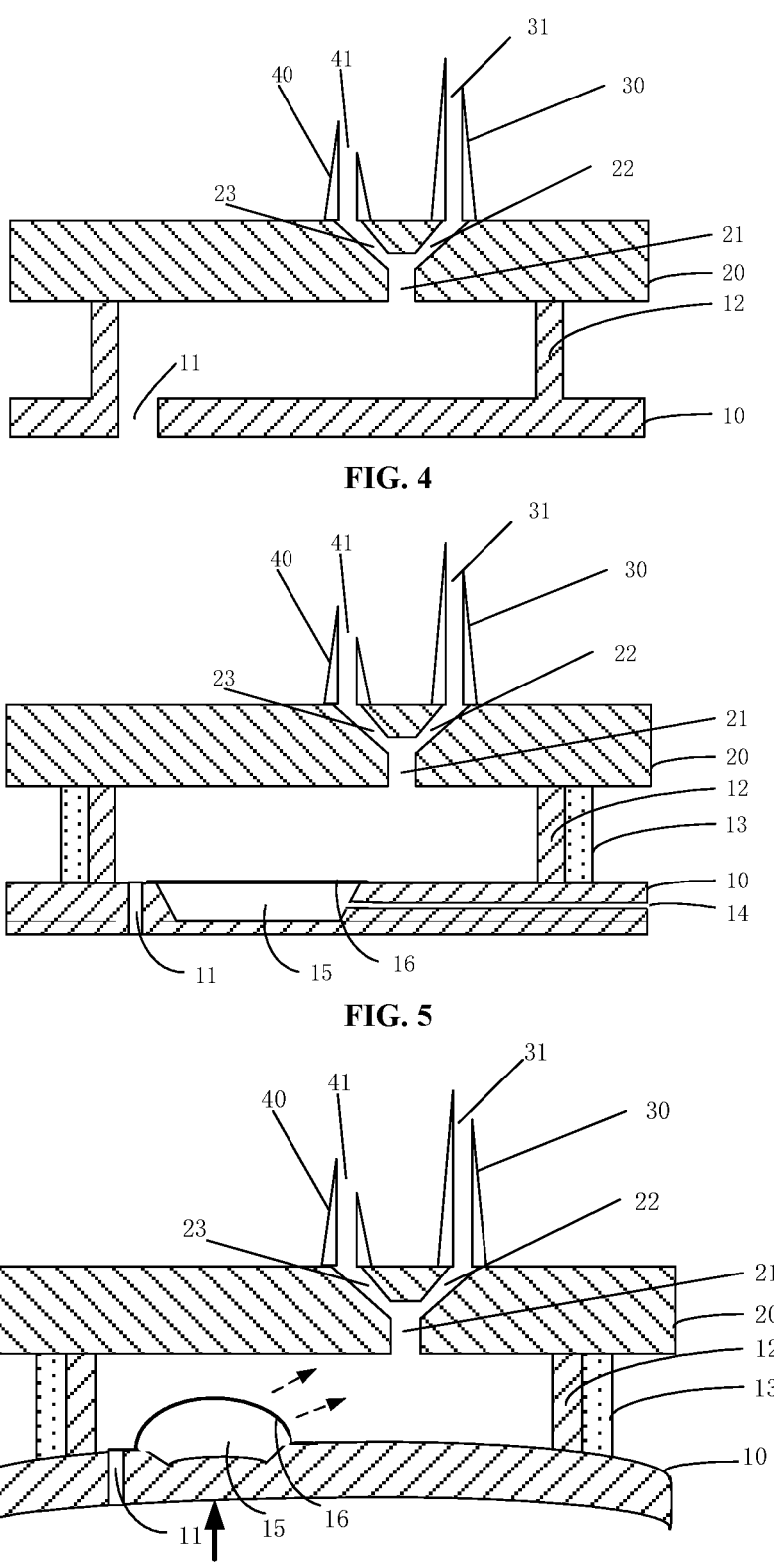
FIG. 4 is a fourth schematic diagram showing a sectional structure of the preparation delivery assembly according to the first embodiment of the present disclosure.
FIG. 5 is a fifth schematic diagram showing a sectional structure of the preparation delivery assembly according to the first embodiment of the present disclosure.
FIG. 6 is a schematic diagram showing a case where an external force is applied to a flexible assembly according to the first embodiment of the present disclosure.

As shown in FIG. 4, a third channel 11 is provided in the first substrate 10, and one end of the third channel 11 is in communication with the first chamber so as to guide the preparation introduced from the other end of the third channel 11 into the first chamber. Specifically, as shown in FIG. 4, the third channel 11 is provided in the first substrate 10 in a direction substantially perpendicular to the first substrate 10.

When selecting materials for the first substrate 10 and the second substrate 20, a flexible material can be selected for either of the substrates. Of course, both of them may be made of a flexible material, which may be, for example, an organic polymer material with better elasticity, such as polydimethylsiloxane.

However, when the assembly is a flexible assembly, the liquid preparation may be blocked in the first chamber during the injection of the preparation due to an external force, which is not conducive to the injection of the blocked part of the preparation in the first chamber. For this consideration, the assembly may have at least one recess 15 provided on a surface of the first substrate 10 proximal to the second substrate 20, and an elastic isolation membrane 16 is provided between the recess 15 and the first chamber such that the recess 15 and the elastic isolation membrane 16 define a second chamber, as shown in FIG. 5. A second channel 14 is further provided in the first substrate 10, and one end of the second channel 14 is in communication with the second chamber, and the other end of the second channel 14 is in communication with the outside so as to introduce air from the outside into the second chamber. Specifically, as shown in FIG. 5, the second channel 14 is provided in the first substrate 10 in a direction substantially parallel to the first substrate 10, and one end of the second channel 14 is in communication with the second chamber, and the other end of the second channel 14 is in communication with the outside so as to introduce air from the outside into the second chamber.

In a specific implementation, the number of the recesses 15 may be greater than one. A valve is provided at the other end of the second channel 14 to control a flow volume of the air entering the second chamber from the outside.

Since each of the needles is a hollow needle and a wall thickness at an end of the needle that is distal to the second substrate 20 may be smaller than a wall thickness at an end of the needle that is proximal to the second substrate 20, it is alternative that an inner wall of the needle is arranged to be substantially perpendicular to the surface of the second substrate 20 that is distal to the first substrate 10 so as to facilitate the penetration of the needle into a human skin.

Different kinds of preparations may have different hydrophilic and hydrophobic properties. When the preparation delivery assembly is used to deliver a preparation, if the preparation to be delivered is hydrophilic in nature and a higher flow rate is required, the inner wall of the needle can be provided to be hydrophilic. If the preparation to be delivered is hydrophilic in nature, but a lower flow rate is required, the inner wall of the needle can be provided to be hydrophobic. If the preparation to be delivered is hydrophobic in nature, but a higher flow rate is required, the inner wall of the needle can be provided to be hydrophilic. If the preparation to be delivered is hydrophobic in nature, but a lower flow rate is required, the inner wall of the needle can be provided to be hydrophobic. In summary, it is necessary to match the hydrophilicity and hydrophobicity of the inner wall of the needle with those of the preparation during the manufacturing of the needle.

Since amounts of the preparation required for different depths of the dermal layer may be different, the needles of different lengths may have different inner diameters. In a specific implementation, the internal diameters of the needles are in a range of 10 micrometers to 80 micrometers. Distances between the respective needles range from 100 micrometers to 500 micrometers. The lengths of the needles are in a range of 25 micrometers to 1000 micrometers. A lateral side of a cross section of the needle taken in a direction perpendicular to the surface of the first or second substrate has an inclination angle of 10 degrees to 25 degrees with respect to a normal direction of the surface of the first substrate 10 or second substrate 20, which is an angle at which a tip of the needle penetrates into the skin.

The preparation delivery assembly will be described hereinafter with reference to FIG. 5 and particular embodiments.

The preparation delivery assembly of this embodiment includes a first substrate 10 and a second substrate 20 for defining a first chamber (also known as a microfluidic flow cavity). The first substrate 10 includes a third channel 11 (also known as a microfluidic inlet), and a side wall 12 (also known as a microfluidic flow cavity retaining wall). The second substrate 20 includes a microfluidic first channel 21 which includes two sub-channels, that is, a first sub-channel 22 and a second sub-channel 23, and two needles (also known as hollow microneedle units). A first needle 30 is a main needle and includes a first microfluidic outlet 31, and a second needle 40 is an auxiliary needle and includes a second microfluidic outlet 41. In addition, a temperature control circuit 13 is provided on an outer side of each side wall 12. In this embodiment, each needle may be replaced with a needle array (also referred to as a microneedle array) for implementation.

The first needle 30 is substantially longer than the second needle 40. Specifically, the length of the first needle 30 is about 100 micrometers to 1000 micrometers, and the length of the second needle 40 is about 25 micrometers to 100 micrometers. Each of the main and auxiliary needles has an internal diameter of about 10 micrometers to 80 micrometers. A distance between the main and auxiliary needles ranges from 100 micrometers to 500 micrometers. A lateral side of a cross section of each of the main and auxiliary needles taken in a direction perpendicular to the surface of the first or second substrate has an inclination angle of 10 degrees to 25 degrees with respect to a normal direction of the surface of the first or second substrate. In a specific implementation, as an alternative embodiment, the preparation delivery assembly may further include needles of three different heights, for example, one main needle and two auxiliary needles. Further, the temperature control circuit 13 may be optionally arranged on one side of the first substrate 10, and the microfluidic inlets (sample inlets) 11 may be provided in the side walls (retaining walls) 12. In addition, the first substrate 10 and the second substrate 20 may be made of a material selected from glass, silicon, polymer, and a metal such as nickel.

In order to be suitable for commercial demands, the preparation delivery assembly may be a flexible assembly in which the first substrate 10 and the second substrate 20 may be made of an organic polymer material with better elasticity, such as polydimethylsiloxane. Therefore, in the preparation delivery assembly of this embodiment, one or more air recesses 15 are additionally provided in the first substrate 10, and a second channel 14 is provided from a side wall of the recess 15 to a side edge of the first substrate 10. The second channel 14 is provided, at its port, with an on-off valve (not shown in the figures) to control air ingress and volume where needed. In addition, an elastic isolation membrane 16 is provided in a position on a surface of the recess corresponding to an opening of the recess 15.

When an external pressure is applied to the flexible assembly, the on-off valve at the port of the second channel 14 is opened such that air is input to the air recess 15. Due to the external force, the air in the recess 15 pushes up the elastic isolation membrane 16, which is equivalent to forming a pneumatic valve that can be opened (the elastic isolation membrane 16 is raised) or closed (the elastic isolation membrane 16 is kept in a horizontal plane) under the action of pressure, thereby realizing the force of changing a liquid flow direction in the first chamber. Therefore, when an external force is applied, the opening of the pneumatic valve causes nearby biological preparation to flow in a direction towards the first channel 21. The elastic isolation membrane 16 used for air-liquid isolation may be selected from commercial low-permeability membranes, such as made of polymethylpentene. Optionally, a plurality of recesses may be provided in the first substrate 10. FIG. 6 is a schematic diagram showing the force acting on the flexible device when an external force is applied.

The advantageous effects of the present design will be explained hereinafter by taking the delivery of various biological preparations as an example.

Human skin is mainly divided into three layers, i.e., an epidermal layer, a dermal layer, and a subcutaneous fat layer. The epidermal layer includes a stratum corneum having a thickness of about 15 micrometers to 20 micrometers, and an active epidermal layer, and the dermal layer contains nerves and blood vessels and has a thickness of about 2000 micrometers.

(1) Cosmetic Application

Polypeptide, an intermediate substance between a protein and an amino acid, can participate in various metabolic processes of a human body, modulate endocrine functions, and can essentially improve a series of conditions in the skin. However, when polypeptides are applied to the epidermal layer of the skin, since its stratum corneum has a unique physiological structure, it is difficult for the polypeptides to pass through the epidermal layer to reach the dermal layer or subcutaneous fat layer so as to be absorbed. As a result, topical polypeptides are less absorbed by the skin. In addition, in oral administration, the polypeptides may be easily degraded and have difficulty in passing through the intestinal mucosa.

By adopting the preparation delivery assembly according to the embodiment of the present disclosure, subcutaneous injection of biological preparations such as polypeptides can be realized, a good diffusion effect can be obtained, and an effective cosmetic effect can be achieved.

(2) Administration for Melanoma

Melanoma, a type of malignant melanoma of the skin, most commonly occurs on the skin of the trunk and extremities, and may also occur in areas that are rarely exposed to the sun. In recent years, melanoma has become the fastest growing malignant tumor among all malignant tumors, with an annual growth rate of 3% to 5%. However, traditional systemic tumor treatment methods are not ideal for melanoma, and receive poor responses. In recent years, new approaches have emerged in the treatment of melanoma, in which site-specific targeted drug therapy has become an effective treatment method in which a targeting drug is delivered directly to the melanoma site through subcutaneous injection, and then released.

The human dermal layer, which can provide not only support but also nutrition for the epidermal layer, is a direct acting layer for the injected subcutaneous drug. However, the thickness of the human dermal layer is about 2000 micrometers. Whether or not a peptide or melanoma targeting drug can be effectively injected into the dermal layer through an in vitro injection device will directly affect the efficacy of these biological preparations in the dermal layer.

Therefore, the needles used in this embodiment include a main needle 30 and an auxiliary needle 40, which have a difference in height. Specifically, the length of the main needle 30 is about 800 micrometers to 1000 micrometers, the length of the auxiliary needle 40 is about 50 micrometers to 100 micrometers, an internal diameter of each of the main and auxiliary needles ranges from 10 micrometers to 30 micrometers, a distance between the main and auxiliary needles is 200 micrometers, and inclination angles of tips of the needles are 15°.

Through the above design of the main and auxiliary needles with a height difference, the biological preparation can successfully reach the dermal layer while the effective injection of the biological preparation into the multiple layers of the dermal layer can be achieved, thereby further improving the effective release of the biological preparation in a target injection area of the skin.

Through the design of inclination of the microneedle tip, it is ensured that the tip of the needle penetrates the epidermal layer smoothly and a tingling sensation is alleviated. The material of the main and auxiliary needles can be selected from silicon, metals, polymers and the like.

In the two applications of the present design as described above, polypeptides and melanoma targeting drugs are basically made by mixing a biocompatible polymer and a cross-linking agent. Taking polypeptides having cosmetic functions as an example, some of the polypeptides are temperature-sensitive, and some of them that exist in a certain form at room temperature change into a gel form as the temperature increases. These biological preparations exist in a liquid form in an in vitro environment which is lower than 35 degrees Celsius, and when they enter a skin tissue environment of a human body at 37 degrees Celsius, their viscosities will gradually increase directly and they will turn into a gel after a period of time, and will be slowly released in targeted skin tissue areas.

Based on this phenomenon, the present design adopts a temperature control circuit 13 provided on an outer side of the side wall 12 to achieve the effect of detecting and regulating the temperature in the first chamber. That is, when the temperature outside the side wall 12 is higher than 35 degrees Celsius, the temperature control circuit 13 will adjust the temperature of the preparation in the first chamber below 35 degrees Celsius by a built-in temperature control circuit of the system to ensure that the biological preparation is in an injectable fluid state in the system.

A fluid is introduced into the preparation delivery assembly through the third channel 11, flows into the first chamber with a capillary force of the fluid in the assembly, and fills the entire first chamber which can hold about 2 μl of the biological preparation.

Then, the biological preparation is formed as a uniformly dispersed solution in the first chamber by an external force, such as, from a mechanical swing table.

The temperature control circuit 13 may include a temperature sensor configured to monitor the temperature in the flow chamber in real time, and a refrigeration unit configured to regulate the temperature when a temperature of an environment, where the microfluidic bioembolic agent delivering assembly is located, is higher than 35 degrees Celsius, so as to ensure an injectable fluid state of the bioembolic preparation in the delivery assembly.

The preparation delivery assembly provided in this embodiment includes the main and auxiliary needles with a height difference design, which can enable effective penetration of the biological preparation through multiple layers. In addition, the assembly incorporates the temperature control circuit to regulate the temperature of the preparation when the temperature of the environment, where the microfluidic bioembolic agent delivering assembly is located, is higher than 35 degrees Celsius, so as to ensure the injectable fluid state of the bioembolic preparation in the delivery assembly.

A second embodiment of the present disclosure provides a preparation delivery device including the preparation delivery assembly provided in the first embodiment, and a storage portion for storing a preparation, which is in communication with the preparation delivery assembly to supply the preparation to the preparation delivery assembly. In a specific implementation, a third channel 11 may be provided in the side wall on either side of the first chamber, or in the first substrate 10, to communicate with the storage portion, and the specific arrangement of the third channel 11 is not limited thereto. The structure of the preparation delivery assembly in the first embodiment will not be described again.

Figure 7:
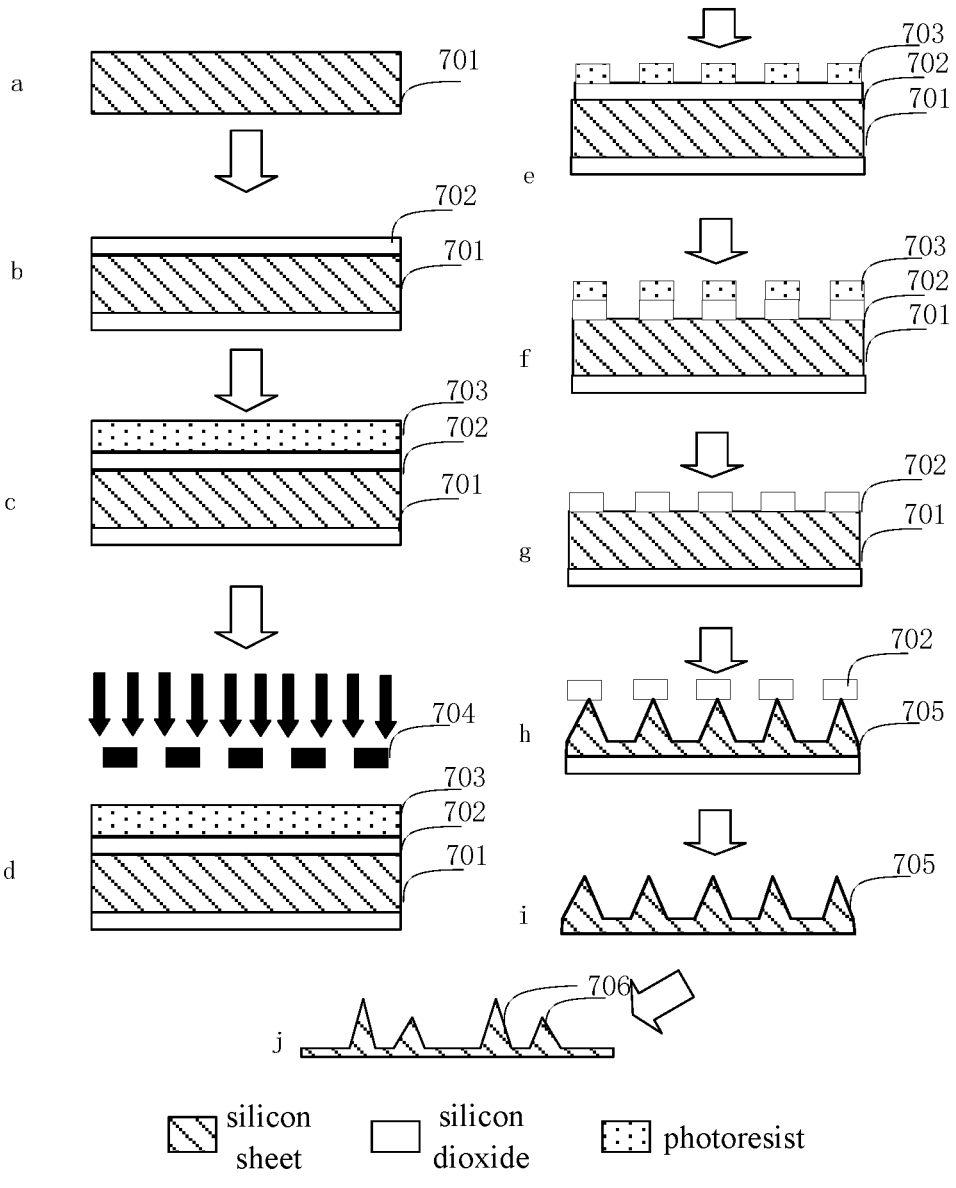
FIG. 7 is a schematic diagram showing steps of a method for fabricating a needle array in the preparation delivery assembly according to a third embodiment of the present disclosure.

A third embodiment of the present disclosure provides a method for fabricating one or more needle arrays in a preparation delivery assembly. There may be various materials that can be used for the needle array(s) of the assembly, including silicon, glass, polymers, and metals such as nickel and stainless steel. Silicon will be taken as an example of the material of the needle in the following description of a method for fabricating the one or more needle arrays, a flow of which is schematically shown in FIG. 7, where (a) to (j) show states of the substrate in corresponding stages of the method. The method includes the following steps.

(1) A protective film 702 is deposited on a first side and a second side of a substrate sheet 701.

This process is schematically illustrated in detail through the stages (a), (b), and (c) of FIG. 7, which are described below.

In stage (a), the substrate sheet 701 is prepared. A substrate sheet made of silicon and having a thickness of about 1200 micrometers to 1500 micrometers is adopted, and washed and dried for use.

In stage (b), the protective film 702 made of silicon dioxide or silicon nitride is deposited on both surfaces of the substrate sheet 701.

In stage (c), a photoresist 703 (liquid or dry film) is applied on either surface (for example, an upper surface as shown in FIG. 7) of the substrate sheet 701 on which the protective film 702 has been deposited, and then dried to form a film.

(2) Through a first patterning process, a pattern of the needle array(s) is formed on the protective film 702 on the first side (i.e., the side of the upper surface) of the substrate sheet 701.

This process specifically includes stages (d), (e), (f), and (g) in FIG. 7.

Among them, the stage (d) shown in FIG. 7 is a process of making a mask. The pattern of the needle array(s) is formed on a mask substrate 704 by using a piece of glass or a film, and a part of the protective film 702 corresponding to an outline of a pattern of each needle on the mask substrate should be removed.

Thereafter, using the pattern of the needle array(s) formed by the protective film 702 as the mask, a shape of the needle array(s) 705 is formed on the substrate sheet 701 by the first patterning process.

This process is schematically illustrated in detail in the stages (e) and (f) of FIG. 7. The stage (e) is a process of exposing the substrate sheet 701 coated with the photoresist 703 by using the mask substrate, in which one or both sides of the substrate sheet 701 to which the photoresist 703 has been applied are exposed (here, a single-sided exposure is illustrated in FIG. 7). Stage (f) is a development process in which trifluoromethane or tetrafluoromethane is used to dry-etch a portion of the silicon dioxide or silicon nitride protective film 702 that is not protected by the photoresist 703 to form a desired shape of the needle array(s) 705.

Thereafter, in stage (g), the photoresist 703 is removed with a NaOH or KOH solution.

(3) Through a second patterning process, ion bombardment is performed on the substrate sheet 701 having the form of the needle array(s) 705, from which the protective film 702 has been removed, by controlling an intensity and time of ion bombardment in each predetermined area, so as to form the needle arrays of different heights.

This process is schematically illustrated in detail in stages (h), (i), and (j) shown in FIG. 7, which are explained below.

In stage (h), through the second patterning process, a portion of the substrate sheet 701 that is not protected by the silicon dioxide or silicon nitride protective film 702 is wet-etched to form a basic form of the needle array(s) 705 on the substrate sheet 701.

In stage (i), the remaining silicon dioxide or silicon nitride protective film 702 is removed by, for example, wet cleaning or dry etching to obtain the substrate sheet 705 having the basic form of the needle array(s).

In stage (j), the needle array(s) is bombarded with ions, such as argon ions, and the intensity and time of ion bombardment in different areas are accurately controlled to form needles 706 having different heights.

When forming the needle array(s), since the size of each of the needles is small, other special processing techniques such as air jet, water jet or explosive formation may be used to form the needle array(s) in a direction perpendicular to the substrate sheet.

After the needle array(s) has been formed, it can be further corroded and polished such that bodies of the needles are smoother and tips thereof are sharper, and the height difference between the main hollow needle unit and the auxiliary hollow needle unit can be further accurately controlled.

After the needle array(s) has been formed, the degree of hydrophilicity/hydrophobicity of surfaces of the needles in the needle array(s) can be treated by oxygen plasma treatment and chemical surface treatment, so that a needle unit can realize the drainage of a specific biological preparation.

In addition, although exemplary embodiments have been described herein, the scope of the present disclosure includes any and all embodiments based on this disclosure having equivalent elements, modifications, omissions, combinations (e.g., solutions where various embodiments overlap), adaptations, or changes. Elements in the claims will be interpreted broadly based on the language used in the claims, and are not limited to the examples described in this description or used during the implementation of this application, and these examples will be interpreted as non-exclusive. Accordingly, this description and the examples are intended to be regarded as illustrative only, and the true scope and spirit of the present disclosure are indicated by the following claims and all their equivalents.

The above description is intended to be illustrative, and not restrictive. For example, the above examples (or one or more of solutions of them) can be used in combination with each other. For example, those skilled in the art can use other embodiments upon reading the above description. In addition, in the above-described embodiments, various features may be grouped together to simplify the present disclosure. This should not be construed as an intent that an unclaimed, disclosed feature is essential for any claim. Rather, the subject matter of the present disclosure may have features which are less than all the features of a disclosed particular embodiment. Thus, the following claims are hereby incorporated into the detailed description as examples or embodiments, wherein each claim is independently taken as a separate embodiment, and it is considered that these embodiments can be combined with each other in various combinations or arrangements. The scope of the disclosure should be determined with reference to the appended claims and all equivalents to which these claims are entitled.

The above are some optional embodiments of the present disclosure. It should be noted that the present disclosure is not limited to these specific embodiments, and several improvements and modifications can be made by those of ordinary skill in the art on the basis of the ideas of the present disclosure, and these improvements and modifications should also be considered as falling within the scope of this disclosure.

What is claimed is:

1. A preparation delivery assembly, comprising:

a first substrate, a second substrate, and at least two needles of different lengths, each of the needles is a hollow needle having a hollow structure;

wherein two side walls are provided between the first substrate and the second substrate to define a first chamber for containing a preparation by the first substrate, the second substrate, and the two side walls;

at least one first channel that is in communication with the first chamber is provided in the second substrate in a direction substantially perpendicular to the second substrate; and the needles are arranged on a surface of the second substrate distal to the first substrate, and each of the needles is in communication with the first chamber through the at least one first channel to deliver the preparation, wherein a third channel is provided in the first substrate in a direction substantially perpendicular to the first substrate, and one end of the third channel is in communication with the first chamber so as to guide the preparation introduced from the other end of the third channel into the first chamber;

wherein at least one of the first and second substrates is made of a flexible material;

wherein at least one recess is provided on a surface of the first substrate proximal to the second substrate, and an elastic isolation membrane is provided between the recess and the first chamber to define a second chamber by the recess and the elastic isolation membrane; and a second channel is further provided in the first substrate in a direction substantially parallel to the first substrate, and one end of the second channel is in communication with the second chamber, and the other end of the second channel is in communication with outside so as to introduce air from the outside into the second chamber;

wherein when external pressure is applied to the assembly, a valve at the other end of the second channel is opened to introduce air into the second chamber, and the air in the second chamber pushes up the elastic isolation membrane, so that the preparation flows towards the first channel.

2. The assembly according to claim 1, wherein the at least one first channel comprises a plurality of sub-channels, each of the sub-channels corresponds to one length of needle among the at least two needles of different lengths; wherein one end of each of the plurality of sub-channels is interconnected within the second substrate and extends to a surface of the second substrate facing the first substrate, and the other end of each of the plurality of sub-channels extends to the corresponding needle respectively.

3. The assembly according to claim 1, further comprising: a temperature control circuit configured to sense a temperature of the preparation contained in the first chamber, and adjust the temperature of the preparation when it is outside an allowable range.

4. The assembly according to claim 1, wherein the number of the recesses is greater than one.

5. The assembly according to claim 1, wherein an inner wall of the needles and the surface of the second substrate distal to the first substrate are substantially perpendicular to each other.

6. The assembly according to claim 5, wherein hydrophilicity and hydrophobicity of the inner wall of the needles match those of the preparation.

7. The assembly according to claim 1, wherein the needles of different lengths have different inner diameters.

8. The assembly according to claim 1, wherein inner diameters of the needles are in a range of 10 micrometers to 80 micrometers.

9. The assembly according to claim 1, wherein distances between the respective needles range from 100 micrometers to 500 micrometers.

10. The assembly according to claim 1, wherein the lengths of the needles are in a range of 25 micrometers to 1000 micrometers.

11. The assembly according to claim 1, wherein a lateral side of a cross section of the needles taken in a direction perpendicular to the surface of the first or second substrate has an inclination angle of 10 degrees to 25 degrees with respect to a normal direction of the surface of the first or second substrate.

12. A preparation delivery device, comprising a preparation delivery assembly, and a storage portion for storing a preparation, the storage portion is in communication with the preparation delivery assembly to supply the preparation to the preparation delivery assembly, wherein the preparation delivery assembly comprises:

a first substrate, a second substrate, and at least two needles of different lengths, each of the needles is a hollow needle having a hollow structure;

wherein two side walls are provided between the first substrate and the second substrate to define a first chamber for containing a preparation by the first substrate, the second substrate, and the two side walls;

at least one first channel that is in communication with the first chamber is provided in the second substrate in a direction substantially perpendicular to the second substrate; and the needles are arranged on a surface of the second substrate distal to the first substrate, and each of the needles is in communication with the first chamber through the at least one first channel to deliver the preparation, wherein a third channel is provided in the first substrate in a direction substantially perpendicular to the first substrate, and one end of the third channel is in communication with the first chamber so as to guide the preparation introduced from the other end of the third channel into the first chamber;

wherein at least one of the first and second substrates is made of a flexible material;

wherein at least one recess is provided on a surface of the first substrate proximal to the second substrate, and an elastic isolation membrane is provided between the recess and the first chamber to define a second chamber by the recess and the elastic isolation membrane; and a second channel is further provided in the first substrate in a direction substantially parallel to the first substrate, and one end of the second channel is in communication with the second chamber, and the other end of the second channel is in communication with outside so as to introduce air from the outside into the second chamber;

wherein when external pressure is applied to the assembly, a valve at the other end of the second channel is opened to introduce air into the second chamber, and the air in the second chamber pushes up the elastic isolation membrane, so that the preparation flows towards the first channel.

13. The device according to claim 12, wherein the at least one first channel comprises a plurality of sub-channels, each of the sub-channels corresponds to one length of needle among the at least two needles of different lengths; wherein one end of each of the plurality of sub-channels is interconnected within the second substrate and extends to a surface of the second substrate facing the first substrate, and the other end of each of the plurality of sub-channels extends to the corresponding needle respectively.

14. The device according to claim 12, wherein the preparation delivery assembly further comprises:

a temperature control circuit configured to sense a temperature of the preparation contained in the first chamber, and adjust the temperature of the preparation when it is outside an allowable range.

15. The device according to claim 12, wherein the number of the recesses is greater than one.

* * * * *